United States Patent [19]

Hampson

[11] 4,327,735

[45] May 4, 1982

[54] CATHETER ASSEMBLY

[75] Inventor: James Hampson, Lauderhill, Fla.

[73] Assignee: Cordis Corporation, Miami, Fla.

[21] Appl. No.: 199,653

[22] Filed: Oct. 22, 1980

[51] Int. Cl.$^3$ .............................................. A61M 25/00

[52] U.S. Cl. .............................. 128/348; 128/DIG. 9

[58] Field of Search ................................ 128/348–350, 128/214.4, 207.14, 262, DIG. 9

[56] References Cited

U.S. PATENT DOCUMENTS

| | | | |
|---|---|---|---|
| 1,190,549 | 12/1914 | Schellberg . | |
| 3,050,066 | 8/1962 | Koehn | 128/349 |
| 3,154,080 | 10/1964 | Rowan | 128/349 |
| 3,335,723 | 8/1967 | Waldman | 128/214.4 |
| 3,421,509 | 1/1969 | Fiore | 128/349 |
| 3,444,860 | 5/1969 | Harrell | 128/349 R X |
| 3,515,137 | 6/1970 | Santomieri | 128/214.4 |
| 3,556,294 | 1/1971 | Walck | 206/63.2 |
| 3,592,192 | 7/1971 | Harautuneian | 128/214.4 |
| 3,595,230 | 7/1971 | Reynolds | 128/348 |
| 3,605,752 | 9/1971 | Schlesinger | 128/349 |
| 3,677,244 | 3/1972 | Blumberger | 128/214.4 |
| 3,766,915 | 10/1973 | Rychlik | 128/214.4 |
| 3,783,870 | 1/1974 | Schachet | 128/276 |
| 3,854,483 | 12/1974 | Powers | 128/349 |
| 3,861,395 | 1/1975 | Taniguchi | 128/349 |
| 3,894,540 | 7/1975 | Bonner | 128/349 R |
| 3,898,993 | 8/1975 | Taniguchi | 128/349 |
| 3,902,500 | 9/1975 | Dryden | 128/349 R X |
| 3,934,721 | 1/1976 | Juster | 206/364 |
| 4,062,363 | 12/1977 | Bonner | 128/349 R |
| 4,170,996 | 10/1979 | Wu | 128/349 |
| 4,213,461 | 7/1980 | Pevsner | 128/348 |

FOREIGN PATENT DOCUMENTS

| | | | |
|---|---|---|---|
| 1170586 | 5/1964 | Fed. Rep. of Germany | 30/17 |
| 1174397 | 12/1969 | United Kingdom | 128/349 R |

*Primary Examiner*—Dalton L. Truluck
*Attorney, Agent, or Firm*—Kenway & Jenney

[57] ABSTRACT

A catheter assembly is disclosed in which there is provided a transparent collapsible sleeve connected and sealed at one end to a hollow tube provided with a socket for the reception of a catheter introducer, the collapsible sleeve terminating at its other end in an O-ring sealingly and slidably engaged with a substantially rigid hollow tube through which a catheter slides, the tube serving to guide the catheter through the sleeve and into the introducer. After the catheter has been positioned in a patient the rigid tube may be removed from the collapsible sleeve, the O-ring then automatically moving into sealing engagement with the exterior of the catheter.

3 Claims, 3 Drawing Figures

12 10 18 16 20 24
24 14 22

CATHETER ASSEMBLY

BACKGROUND OF THE INVENTION

It has long been recognized that catheters lose their sterility either in the process of insertion or thereafter. There have been many proposed solutions for the problem, an example of which is U.S. Pat. No. 3,894,540 to F. J. Bonner, Jr. dated July 15, 1975. That patent, and others, disclose the use of a collapsible protective sleeve surrounding the catheter, and while such devices have not been unsuccessful, they do require extremely skillful handling and are not particularly designed for adjustment after the initial insertion into the body of the patient. Such adjustments are particularly necessary when catheters are inserted into the heart for purposes of measuring its activity. It often happens that when the catheter is originally implanted, its tip lodges in an area of the heart which is not sufficiently sensitive. Consequently such cardiac catheters need to be moved about until the end within the heart lodges in a sufficiently responsive area. Such manipulations often require that the end be moved farther into the body, thus requiring that an additional length of catheter be utilized.

SUMMARY OF THE INVENTION

This invention provides a catheter assembly provided with a collapsible protective sleeve and so arranged that a flexible catheter may be easily advanced through a standard introducer without in any way exposing the catheter to contamination. Moreover, the assembly is also so arranged that the catheter may be further advanced into the body at any time, again without exposing the catheter to the risk of contamination. The assembly is provided with a relatively rigid hollow tube maintained in sealing relationship to the collapsible sleeve and dimensioned to receive and guide a catheter. As the catheter is passed through the introducer and into the body of the patient the sleeve collapses to the extent the catheter is moved into the body. Thereafter the rigid tube may be removed from the sleeve and the sleeve then automatically becomes sealed to the exterior of the catheter. This arrangement not only protects the catheter from contamination, but is extremely simple to use.

BRIEF DESCRIPTION OF THE DRAWINGS

Other objects and advantages of this invention will be more readily understood and appreciated from the following detailed description of a preferred embodiment shown in the accompanying drawing.

DESCRIPTION OF THE PREFERRED EMBODIMENT

Figure 1:
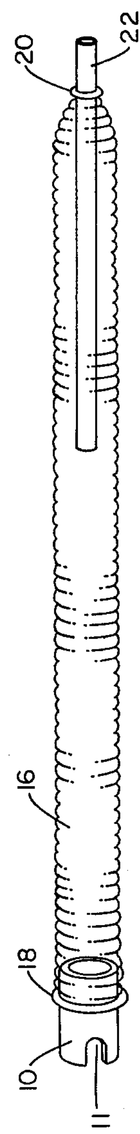
FIG. 1 is a view in side elevation of the assembly of the invention prior to its connection to an introducer and prior to the addition of a catheter.
Figure 2:
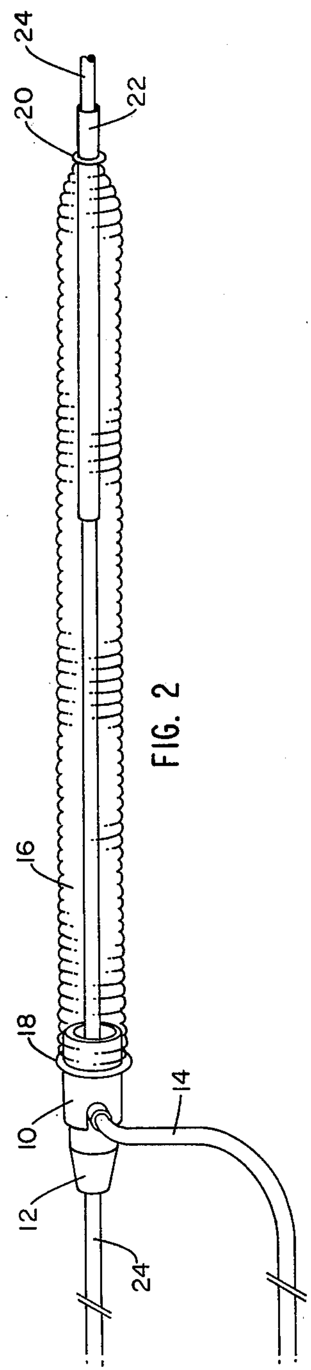
FIG. 2 is a view in side elevation of the catheter assembly showing the catheter in place and the assembly connected to an introducer.

As shown in the drawings the catheter assembly is organized about a cylindrical hollow tube 10 of metal, preferably stainless steel, having a socket 11 by means of which the tube 10 may be connected to an introducer 12. The introducer 12 is standard and those skilled in the art will readily understand that no detailed description of it is required. The introducer 12 has the usual side port 14.

Secured to the other end of the tube 10 is a collapsible sleeve 16 made of a waterproof material such as cellophane or other suitable transparent plastic. The sleeve 16 may be provided with accordion pleats to facilitate its ability to collapse or be extended. The sleeve 16 is secured to the tube 10 by means of a rubber O-ring 18, although any suitable means may be utilized, to secure the end of the tube 16 to the tube 10, such, for example, as a suitable adhesive.

At its other end the sleeve 16 carries another O-ring 20 which tightly grips and seals a hollow fairly rigid tube 22. The tube 22 is dimensioned to receive a catheter 24 which slides through the tube 22, through the sleeve 16, and then through the introducer, thus permitting insertion of the catheter into an artery or other organ of a patient under treatment.

Figure 3:
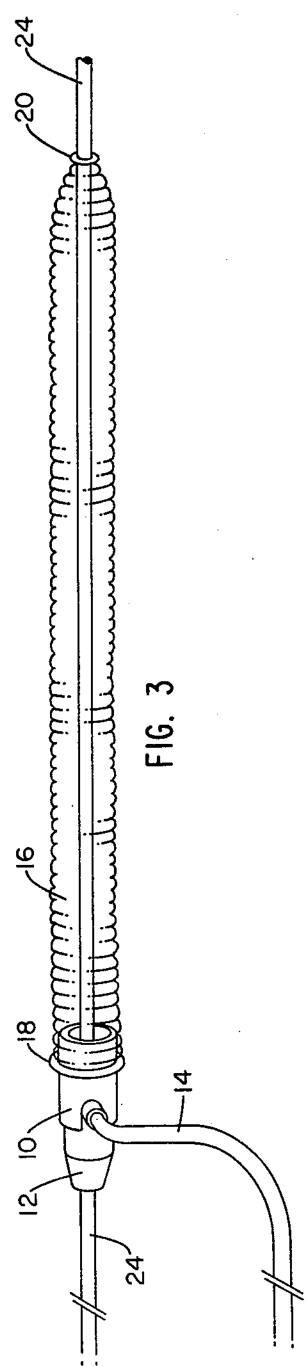
FIG. 3 is a view in side elevation of the catheter assembly subsequent to the removal of the guide tube.

As shown in FIG. 3 the tube 22, after the catheter has been inserted, may be removed by sliding it through the O-ring 20 and out onto the remaining body of the catheter 24. As the tube 22 leaves the O-ring 20, the O-ring contracts about the surface of the catheter 24 and is in sealing engagement with it. Consequently the catheter within the sleeve 16 is completely sealed and not subject to contamination. If it becomes necessary to reposition the catheter after its initial insertion, it is only necessary for the physician to grasp the catheter, preferably at the O-ring 20 and move it in or out as required. Again, the adjustment operation in no way exposes the catheter to contamination but maintains it in sterile condition.

When the tube 22 has been removed from the sleeve 16, it can be left in place upon the portion of the catheter which remains outside the sleeve 16. However, the tube 22 may be provided with a longitudinal slit so that it can be stripped off the catheter after it leaves the sleeve 16.

While the embodiment herein shown and described is presently considered to be preferred, it will be understood that various modifications and improvements may be made therein, and it is intended to cover in the appended claims all such modifications and improvements as fall within the true spirit and scope of the invention.

I claim:

1. A catheter assembly comprising a longitudinally collapsible sleeve of flexible waterproof material, an introducer socket, means securing one end of said sleeve to said introducer socket, a relatively rigid tube slidably mounted in said sleeve, an O-ring secured to the other end of said sleeve and slidably engaging the outer surface of said tube in sealing relation thereto, and a relatively flexible catheter mounted to slide through said tube, sleeve and introducer socket, whereby said catheter may be moved into position in the body of a patient, the tube may be withdrawn from the sleeve and the O-ring thereupon sealingly engages the sleeve with the catheter.

2. A catheter assembly comprising an elongated flexible tubular catheter, an introducer socket, a relatively rigid tubular member slidably embracing a portion of said catheter, a collapsible sleeve of flexible material secured and sealed to the end of said introducer socket, and a resilient O-ring secured to and sealed to the end of said sleeve, said O-ring serving to sealingly and slidably connect said sleeve to said tubular member, whereby said catheter may be slid through said tubular member and said introducer socket and positioned within the body of a patient, said tubular member may be retracted from said sleeve through said O-ring, and whereby said O-ring then sealingly engages the external surface of said catheter.

3. A catheter assembly comprising a longitudinally collapsible sleeve of flexible waterproof material, an introducer socket, means securing one end of said sleeve to the end of said introducer socket, a relatively rigid tube slidably mounted in said sleeve, resilient clamping means secured to the other end of said sleeve and slidably engaging the outer surface of said tube in sealing relation thereto, and a relatively flexible catheter mounted to slide through said tube, sleeve and introducer socket, whereby said catheter may be moved into position in the body of a patient, the tube may be withdrawn from the sleeve and the resilient clamping means thereupon sealingly connects the sleeve to the catheter.

* * * * *